United States Patent [19]

Micetich et al.

[11] 4,327,222

[45] Apr. 27, 1982

[54] 3,4-DIARYLISOXAZOL-5-ACETIC ACIDS AND PROCESS FOR MAKING SAME

[75] Inventors: Ronald G. Micetich, Sherwood Park; Chia-Cheng Shaw, Edmonton; Ram B. Rastogi, Beaconsfield, all of Canada

[73] Assignee: CDC Life Sciences Inc., Toronto, Canada

[21] Appl. No.: 190,060

[22] Filed: Sep. 23, 1980

[30] Foreign Application Priority Data

Oct. 5, 1979 [CA] Canada ............................ 337097

[51] Int. Cl.$^3$ ................... C07D 261/08; A61K 31/42
[52] U.S. Cl. ................... 548/247; 424/272
[58] Field of Search ......................... 548/247

[56] References Cited

U.S. PATENT DOCUMENTS 3,891,635 6/1975 Henniger .
4,010,264 3/1977 Henniger .

FOREIGN PATENT DOCUMENTS 1164510 9/1969 United Kingdom .

OTHER PUBLICATIONS

Micetich, Can. J. Chem. 48, 2006 (1970).
Chem. Abs. 70, 20054u (1969).
Chem. Abs. 77, 48483b (1972).
Chem. Abs. 80, 108511h and 108513k.
Beam et al., J. Org. Chem. 35, 1806 (1970).
Chemistry of Carbon Compounds, E. H. Rodd, Ed., vol. III, 1168–1171, New York 1956.
Winter et al., Proc. Soc. Exp. Biol. Med. 111, 544 (1962).
Winder et al., J. Pharmacol. Exp. Therap. 138, 405 (1962).
Siegmund et al., Proc. Soc. Exp. Biol. Med. 95, 729 (1957).
Sofia et al., J. Pharm. Sci. 64, 1321 (1975).
Litchfield and Wilcoxon, J. Pharmacol. Exp. Therap. 96, 99 (1949).

*Primary Examiner*—Anton H. Sutto
*Attorney, Agent, or Firm*—Cushman, Darby & Cushman

[57] ABSTRACT

3,4-Diarylisoxazol-5-acetic acids of the formula $$R^1R^2(Ar^1)\underset{N\diagdown O}{\overset{\phantom{x}}{\diagup\!\!\!\diagdown}}\underset{CHR^5-COOH}{\overset{(Ar^2)R^3R^4}{\phantom{x}}} \quad 1$$

in which $Ar^1$ and $Ar^2$ are the same or different and are selected from phenyl and naphthyl, $R^1$, $R^2$, $R^3$, and $R^4$ are the same or different and are selected from hydrogen, halogen, trifluoromethyl, lower alkyl, and lower alkoxy, and $R^5$ is selected from hydrogen, lower alkyl, and lower alkoxy. The compounds have anti-inflammatory, analgesic, and anti-pyretic activities and a low order of toxicity, and methods for their preparation and use are also disclosed.

24 Claims, No Drawings

3,4-DIARYLISOXAZOL-5-ACETIC ACIDS AND PROCESS FOR MAKING SAME

The present invention relates to 3,4-diarylisoxazol-5-acetic acids of the formula 1

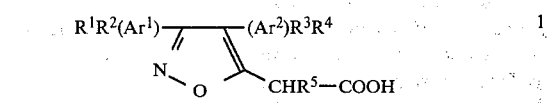

in which $Ar^1$ and $Ar^2$ are the same or different and are selected from phenyl and naphthyl, $R^1$, $R^2$, $R^3$, and $R^4$ are the same or different substituents attached to $Ar^1$ and $Ar^2$ and are selected from hydrogen, halogen, trifluoromethyl, lower alkyl, and lower alkoxy, and $R^5$ is selected from hydrogen, lower alkyl, and lower alkoxy, to a process for preparing said acids, and to the pharmaceutically acceptable salts of said acids. The term "lower" denotes the presence of 1–4 carbon atoms in a straight or branched chain.

BACKGROUND OF THE INVENTION

3-Methyl- and 3-phenylisoxazol-5-acetic acids have been described by Micetich in Can. J. Chem. 48, 2006(1970), and the latter compound as well as its ethyl ester have also been reported by Kano et al., Jap. Pat. 6,814,216, June 15, 1968, Chem. Abs. 70, 20054u(1969). 3,4-Disubstituted isoxazol-5-acetic acids and 5-α-substituted acetic acids have been described in German Offenlegumgsschriften 2,155,081 (May 10, 1072) and its Divisions 2,166,467 and 2,166,468 (both Feb. 14, 1974), Chem. Abs. 77, 48483b(1972), 80, 108511h(1974), and 80, 108513k(1974), respectively, and equivalent to U.S. Pat. Nos. 3,891,635, June 24, 1975, and 4,010,264, Mar. 1, 1977; however, the compounds disclosed therein are distinguished from the compounds of this invention in having an aryl substituent only in position 3 while the substituent in position 4 is not an aryl group and is selected from H, lower alkyl, COOH, $CONH_2$, CN, $NH_2$, and Cl.

With regard to processes disclosed in the Prior Art it should be noted that an unambiguous process for preparing 3,5-diaryl- and 3,4,5-triarylisoxazoles has been described by Beam et al. in J. Org. Chem. 35, 1806(1970), and that the conversion of 5-methylisoxazoles to the corresponding isoxazol-5-acetic acids and -5α-alkyl-acetic acids has been reported by Micetich, cited above.

SUMMARY DESCRIPTION OF THE INVENTION

The compounds of this invention of formula 1 are conveniently prepared by a modification of the method described by Beam et al. cited above. An aryl-(aryl-substituted methyl)-ketone of formula 2, e.g. desoxybenzoin or desoxyanisoin, is converted to the corresponding oxime, 3, and the latter compound is treated with 2 molar equivalents of n-butyllithium in an inert solvent under nitrogen at temperatures within the range of −15° to 5° C., preferably at about 0° C., to obtain the corresponding dilithio salt in the reaction mixture. A lower alkyl acetate or lower alkyl (lower alkoxy)acetate is added (0.5 molar equivalents); the mixture is stirred for 10–120 minutes at about 0° C., acidified with a mineral acid, and heated, preferably to refluxing, for 1–3 hours. Cooling, extraction with a water-immiscible solvent, evaporation of the latter, and crystallization yields the corresponding 3,4-diaryl-5-methyl- or 3,4-diaryl-5-(lower alkoxy)methylisoxazole (4) respectively. The latter compound is treated under nitrogen with one molar equivalent or with a slight molar excess, preferably about 1.1 molar equivalents, of n-butyllithium in an inert solvent with cooling to a temperature below −50° C. for 1–3 hours, and the resulting mixture is treated with dry ice. Dissolving the reaction mixture in water, acidification, extraction with a water-immiscible solvent, evaporation of the latter, and crystallization yields the corresponding 3,4-diarylisoxazol-5-acetic acid or 3,4-diarylisoxazol-5α-(lower alkoxy) acetic acid, respectively, i.e. the compounds of formula 1 in which $Ar^1$, $Ar^2$, $R^1$, $R^2$, $R^3$, and $R^4$ are as defined above and $R^5$ is hydrogen or lower alkoxy, respectively.

When it is desired to obtain the compounds of formula 1 in which $R^5$ is lower alkyl, the corresponding 3,4-diarylisoxazol-5-acetic acid, i.e. the corresponding compound of formula 1 in which $R^5$ is hydrogen, is treated with 2 molar equivalents of n-butyllithium followed by treatment with a lower alkyl halide in which the halogen has an atomic weight greater than 19, in the general manner described by Micetich cited above. Working up in a manner similar to that described above yields the corresponding 3,4-diarylisoxazol-5α-(lower alkyl)acetic acid of formula 1 in which $R^5$ is lower alkyl.

The starting materials for the above process, i.e. the aryl-(aryl-substituted methyl)-ketones of formula 2, are either commercially available or are conveniently prepared by conventional methods, e.g. as described in "Chemistry of Carbon Compounds", Ed. E. H. Rodd, Vol. III, pp. 1168–1171, D. Van Nostrand Co., Inc., New York 1956.

The pharmacologically acceptable salts of the free acids of this invention of formula 1 are prepared from said acids by conventional means, e.g. as described in Example 5.

The following formulae in which $Ar^1$, $Ar^2$, $R^1$, $R^2$, $R^3$, $R^4$, and $R^5$ are as defined above and Alk is lower alkyl will illustrate the above sequences of reactions.

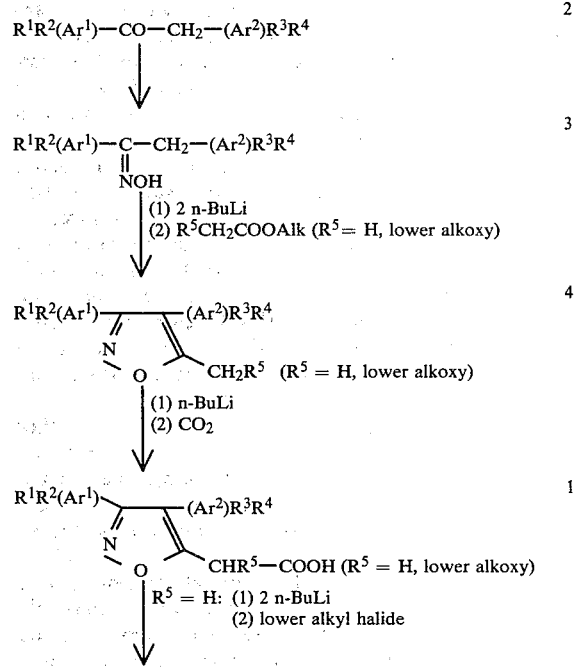

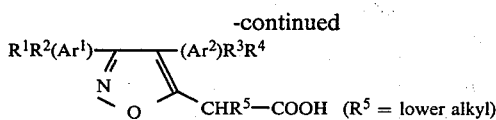

$$\text{CHR}^5\text{---COOH} \quad (R^5 = \text{lower alkyl}) \quad 5$$

DETAILED DESCRIPTION OF THE INVENTION

More specifically, the compounds of this invention of formula 1 in which $Ar^1$, $Ar^2$, $R^1$, $R^2$, $R^3$, and $R^4$ are as defined above and $R^5$ is hydrogen or lower alkoxy are prepared as follows.

An aryl-(aryl-substituted methyl)-ketone of formula 2 is treated with hydroxylamine hydrochloride in an inert solvent, preferably a mixture of a lower alkanol and water in the presence of a strong base, preferably sodium hydroxide, to obtain the corresponding oxime of formula 3 after working up in the conventional manner.

Said last-named oxime is dissolved in an inert solvent, preferably an ether such as dimethoxyethane or a cyclic ether such as tetrahydrofuran (THF) and the solution is cooled to a temperature within the range of −50° C. to 0° C., preferably to about −15° C. Two molar equivalents of a solution of n-butyllithium are then added under nitrogen at such a rate that the temperature of the reaction mixture is maintained between −15° C. and 5° C., preferably as close as possible to 0° C. After completion of the addition the reaction mixture is stirred at −5° C. to 5° C., preferably at about 0° C. for 10–60 minutes to obtain a solution of the corresponding dilithio salt. One half molar equivalent of a cold lower alkyl acetate or lower alkyl (lower alkoxy)acetate of the formula $R^5CH_2COOAlk$ in which $R^5$ is hydrogen or lower alkoxy and Alk is lower alkyl is then added, preferably in small successive portions so as to maintain the temperature of the mixture close to 0° C., the mixture is stirred at −5° C. to 5° C., preferably at about 0° C. for 10–120 minutes. acidified with a mineral acid, preferably hydrochloric acid, and heated to 50°–150° C., preferably to the reflux temperature of the mixture, for 1—3 hours. Cooling to room temperature, separating the aqueous phase and extracting it with ether, combining said extracts with the organic phase, concentrating the resulting solution followed by fractional crystallization gives the corresponding 3,4-diaryl-5-methyl- or -5-(lower alkoxy)methylisoxazole of formula 4 in which $R^5$ is hydrogen or lower alkoxy.

Said last-named compound of formula 4 is dissolved in an inert solvent, preferably an ether such as dimethoxyethane or a cyclic ether such as THF, and is treated with 1.0–1.1 molar equivalents of n-butyllithium at a temperature below −50° C., preferably at about −75° C., in an atmosphere of nitrogen for 1–3 hours. The resulting mixture is reacted with solid carbon dioxide by pouring it on finely powdered dry ice and allowing the reacting mixture to come to ambient temperature with constant agitation. Evaporation of the solvent under reduced pressure and washing the residue with ether gives the lithium salt of the acid of formula 1 in which $R^5$ is hydrogen or lower alkoxy which may be isolated if desired and converted to the free acid by acidification. Alternatively, the reaction mixture is diluted with water, extracted with ether, the aqueous phase cooled in ice, acidified with a mineral acid, preferably hydrochloric acid, extracted with a water-immiscible solvent such as ethyl acetate, and the extracts dried and concentrated, to obtain the corresponding compound of formula 1 in which $Ar^1$, $Ar^2$, $R^1$, $R^2$, $R^3$ and $R^4$ are as defined above and $R^5$ is hydrogen or lower alkoxy.

For the preparation of the compounds of formula 1 in which $R^5$ is lower alkyl the procedure described by Micetich cited above is conveniently employed, as follows.

A compound of formula 1 in which $R^5$ is hydrogen, prepared as described above, in solution in an ether such as dimethoxyethane or preferably in a cyclic ether such as THF, is treated at a temperature below −20° C. with 2 molar equivalents of n-butyllithium. The mixture is stirred at the same temperature in an atmosphere of nitrogen for 20–60 minutes and 1.2–1.7 molar equivalents, preferably 1.5 molar equivalents, of a lower alkyl halide, preferably a lower alkyl bromide or iodide, are added. Agitation is continued for 1–3 hours, the mixture is allowed to come to room temperature, diluted with water, acidified with a mineral acid, extracted with a water-immiscible solvent, the extracts evaporated and the residue crystallized, to obtain the corresponding compound of formula 1 in which $R^5$ is lower alkyl.

The compounds of formula 1 have anti-inflammatory, analgesic, and anti-pyretic properties and have a low order of toxicity. The anti-imflammatory properties are demonstrated in a modification of the test using the carrageenin-induced paw edema described by Winter et al., Proc.Soc.Exp.Biol.Med. 111, 544 (1962) and in the cotton pellet granuloma test described by Winder et al., J. Pharmacol. Exp. Therap. 138, 405 (1962), both in the rat. The analgesic activities are demonstrated in a modification of the phenylquinone-induced muscular writhing test in mice described by Siegmund et al., Proc.Soc.Exp.Biol. 95, 729 (1957). The anti-pyretic properties are demonstrated in rats in the yeast-induced fever test described by Sophia et al., Journal of Pharm.Sciences 64, 1321–1324 (1975). Acute toxicities are determined in rats and in mice and the $LD_{50}$'s are calculated according to the method of Litchfield and Wilcoxon, J.Pharmacol.Exp. Therap. 96, 99 (1949).

The low order of toxicity found for the compounds of this invention of formula 1 and the very high terapeutic indices calculated for those compounds as $LD_{50}$/anti-inflammatory $ED_{50}$ are of particular advantage when considering that anti-inflammatory drugs have to be administered repeatedly over prolonged periods of time.

When one of the compounds of formula 1 is employed as an anti-inflammatory, analgesic, and/or anti-pyretic agent in warm-blooded animals, e.g. in rats, it may be used alone or in combination with pharmaceutically acceptable carriers, the proportion of which is determined by the solubility and chemical nature of the compound, chosen route of administration and standard biological practice. For example, an anti-inflammatory, analgesic, and/or antipyretically effective amount of the compound may be administered orally in solid form containing such excipients as starch, sugar, certain types of clay and so forth. Similarly, such an amount may also be administered orally in the form of solutions or suspensions, or the compound may be injected parenterally. For parenteral administration the compound may be used in the form of a sterile solution or suspension containing other solutes or suspending agents, for example enough saline or glucose to make the solution isotonic; bile salts, acacia, gelatin, sorbitan monoleate, polysorbate 80 (oleate esters of sorbitol and its anhydrides copolymerized with ethylene oxide) and the like.

The dosage of the present compounds of formula 1 will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford anti-inflammatory, analgesically, and/or anti-pyretically effective results without causing any harmful or deleterious side effects and preferably at a level that is in a range of from about 1.0 mg to about 250 mg per kilo per day, although as aforementioned variations will occur. However, a dosage level that is in the range of from about 10 mg to about 100 mg per kilo per day is most desirably employed in order to achieve effective results.

The anti-inflammatory, analgesic, and anti-pyretic activities of the compounds of this invention are well within the range of those of a number of well known anti-inflammatory drugs and are generally superior to those of known 3-arylisoxazol-5-acetic acids. In particular, the compound 3,4-di(p-methoxyphenyl)isoxazol-5-acetic acid described in Example 4 is distinguished by remarkable anti-inflammatory and analgesic activities and by a low order of toxicity, a combination of properties which give a favourable therapeutic index and which make that compound especially advantageous for long-term administration as an anti-inflammatory drug.

The following Examples will further illustrate this invention.

EXAMPLE 1

Desoxyanisoin Oxime

Desoxyanisoin (98%, 52.2 g., 0.2 mole) and hydroxylamine hydrochloride (15.3 g., 0.22 mole) are slurried in a mixture of methanol (300 ml) and water (200 ml) and sodium hydroxide (16 g., 0.4 mole) is added slowly. The mixture is stirred for 15 minutes, then placed in a hot water bath (70° C.) and stirred an additional hour. Methanol is then added to the hot mixture until solution is almost complete, the mixture is filtered and concentrated to remove most of the methanol, then cooled with the addition of ice-water. Filtered, dissolved the resulting solid in ethyl acetate, extracted with brine. Dried the organic layer ($Na_2SO_4$), filtered and concentrated to obtain 53.5 g (98.5%) of the oxime as a yellow solid.

EXAMPLE 2

3,4-Di(p-methoxyphenyl)-5-methylisoxazole

A solution of the oxime (6.78 g., 0.025 mole) from Example 1 in THF (100 ml) is cooled to $-15°$ C. and n-butyllithium (21 ml of 2.4 molar solution, 0.05 mole) is added under nitrogen at such a rate as to maintain the temperature at 0° C. After completion of the addition the mixture is stirred at 0° C. for 30 minutes, cold ethyl acetate (1.1 g., 0.0125 mole) in 15 ml THF is added, the mixture is stirred at 0° C. for 15 minutes, 100 ml of 3 N hydrochloric acid is added, the mixture is refluxed with stirring in an oil-bath at 75° C., cooled and the layers are separated. The aqueous layer is extracted with ether (3×100 ml), the combined organic layers are concentrated and the resulting oil is taken up in methanol (15 ml), cooled and the crystalline desoxyanisoin (1.5 g) removed by filtration. The filtrate is concentrated and the oil taken up in warm ethanol (15 ml). On cooling in a freezer overnight the title compound is obtained as a colourless solid, m.p. 95°–99° C. after recrystallization from ethanol. The nmr ($CDCl_3$) spectrum $\tau$ 7.6 (3H, s, $C_5$-$CH_3$), 6.25 (6H, d, 2 $CH_3O$-), 3.25 to 2.5 (8H, m, aryl H), is consistent with the assigned structure.

EXAMPLE 3

3,4-Di(p-methoxyphenyl)-5-methoxymethylisoxazole

A solution of the oxime (26.77 g., 0.099 mole) from Example 1, in THF (350 ml) is cooled to $-5°$ C. and n-butyllithium (90 ml of 2.22 molar, 0.198 mole) is added under nitrogen at such a rate as to maintain the temperature at 0° C. The reaction mixture is stirred an additional 35 minutes at 0° C. and methyl methoxyacetate (10.3 g., 0.099 moles) in THF (50 ml) is added over a 10 to 15 minute period. The red solution is stirred at 0° C. for 1 hour, 3 N hydrochloric acid (400 ml) is added, the mixture is heated under reflux for 1 hour, cooled and the layers are separated. The aqueous layer is extracted with ether (3×200 mls), the combined organic layers are dried ($Na_2SO_4$), concentrated, and the resulting oil is dissolved in warm ethanol and cooled when 1.6 g. of desoxyanisoin crystallizes out and is filtered off. The mother liquor on concentration gives 30.1 g. of a thick oil the nmr spectrum of which indicates the presence of unreacted starting material. A mixture of the above oil (25 g., 0.076 mole), phosphorus pentoxide (14 g., 0.1 mole) and benzene (200 ml) is heated under reflux with good mechanical stirring for 45 minutes and a light orange solution containing a black gum is obtained. The mixture is filtered hot and concentrated to give 24 g. of a thick oil, and distillation gives the title compound as a thick oil, b.p. 204°–208°/0.1 mm. The nmr ($CDCl_3$) spectrum $\tau$ 6.78 (3H, s, $CH_2OCH_3$), 6.4 (6H, d, 2-$OCH_3$), 5.7 (2H, s, -$CH_2OCH_3$), 3.35 to 2.6 (8H, m, aryl Hs), is in agreement with the assigned structure.

EXAMPLE 4

3,4,-Di(p-methoxyphenyl)isoxazol-5-acetic Acid n-Butyllithium (50 ml of 1.6 molar solution, 80 mmole) is added dropwise to a stirred, cold (dry-ice-acetone bath), solution of 3,4-di(p-methoxyphenyl)-5-methylisoxazol (21.72 g., 73.6 mmole, Ex. 2) in THF (220 ml) under a nitrogen atmosphere. After stirring for 1 hour at $-75°$ C., the red coloured mixture is poured into crushed dry-ice and stirred. The stirred mixture is allowed to warm to room temperature, concentrated, and the residue dissolved in water. The resulting solution is twice extracted with ether, layered with ethyl acetate, cooled in ice and acidified with concentrated hydrochloric acid. The layers are separated and the aqueous layer extracted with ethyl acetate. The combined ethyl acetate layers are dried ($MgSO_4$) and concentrated to give a sticky foam residue. Recrystallization from benzene gives the title compound as a colourless solid, m.p. 142°–143° C. The nmr ($CDCl_3$) spectrum $\tau$ 6.2 (8H, s, d, $CH_3O$ and —$CH_2$—), 3.28 to 2.52 (8H, m, aryl H's), 0.45 (1H, broad, $COOH$) agrees with the assignment.

EXAMPLE 5

Sodium 3,4-Di(p-methoxyphenyl)isoxazol-5α-methoxyacetate

Starting with 3,4-di(p-methoxyphenyl)-5-methoxymethylisoxazole (from Example 3), and using the same procedure as in Example 4, the free acid 3,4-di(p-methoxyphenyl)-5α-methoxyacetic acid is obtained as a thick oil. The oil is dissolved in methanol and treated with one molar equivalent of sodium 2-ethylhexanoate (3 M methanol solution), stirred for 0.5 hours, concentrated and the solid washed well with ether, to give the title compound. The nmr ($D_2O$) spectrum δ6.25 to 7 (m, 8H, aryl H), 4.6 (s, DOH and —C$\underline{H}$), 3.3 (ss, 6H, aryl OC$\underline{H}_3$) 3.05 (s, 3H, CHOC$\underline{H}_3$), is in agreement with the assigned structure.

EXAMPLE 6

3,4-Diphenylisoxazol-5-acetic Acid

Desoxybenzoin is converted to the corresponding oxime in the same manner as described in Example 1, and the latter oxime is treated with 2 molar equivalents of n-butyllithium followed by treatment with ethyl acetate in the same manner as described in Example 2, to obtain 3,4-diphenyl-5-methylisoxazole. The latter compound is treated with 1.0–1.1 molar equivalents of n-butyllithium followed by treatment with dry ice in the same manner as described in Example 4, to obtain the title compound with m.p. 153°–157° C. after recrystallization from benzene, and with an nmr spectrum, (acetone $d_6$), δ7.4 (br, s, 11H, aryl H and COO$\underline{H}$), 3.9 (s, 2H, —C$\underline{H}_2$), in agreement with the assigned structure.

EXAMPLE 7

The anti-flammatory, analgesic, and anti-pyretic properties as well as the acute toxicities of a number of well-known anti-inflammatory drugs are compared with the data obtained for the known compounds 3-phenylisoxazol-5-acetic acid and 3-(p-methoxyphenyl-)isoxazol-5-acetic acid and for the title compounds of Examples 4, 5, and 6. The data are shown in the following Table 1, and it will be noted that particularly the title compound of Example 4 has anti-inflammatory and analgesic activites which are well within the range of the same activities shown for a number of established anti-inflammatory drugs and are markedly superior to the activities of known 3-arylisoxazol-5-acetic acids.

TABLE 1

| Compound | $ED_{50}$ p.o. (mg/kg) Anti-inflammatory (Carrageenin) | Analgesic (Phenylquinone) | Anti-Pyretic (Yeast) | Acute Toxicity (g/kg) p.o. |
|---|---|---|---|---|
| Indomethacin | 7–9 | <1 | 3–5 | 0.027 (Rats) |
| Naproxen | 10–12 | 7.5–10 | 15–20 | 0.347 (Rats) |
|  |  |  |  | 0.830 (Mice) |
| Ibuprofen | 15–30 | 15–25 | 15 | 1.25 (Rats) |
| Sulindac | 20–30 | 7.5–10 | 7.5–10 | — |
| Aspirin | 60–90 | 70–100 | — | 1.74 (Rats) |
| Mefenamic Acid | 45–55 | 7.5–10 | 7.5–10 | — |
| 3-Phenylisoxazol-5-acetic Acid | 70–80 | 60–90 | >135 | 1.5 (100% mortaility, rats) |
| 3-(p-Methoxyphenyl)-isoxazol-5-acetic Acid | >135 | 60 | >120 |  |
| 3,4-Diphenylisoxazol-5-acetic Acid | 120 |  | 120 | $LD_{50}$(mice) 0.67g/kg |
| 3,4-Di(p-methoxyphenyl)-isoxazol-5-acetic Acid* | 25–40 | 1.8 | >120 | $LD_{50}$(mice) 1.0g/kg |
| Sodium 3,4-Di(p-methoxyphenyl)isoxazol-5α-methoxyacetate | 120 | 60 | >120 |  |

*Also active in anti-granuloma test.

We claim:

1. A compound of the formula 1

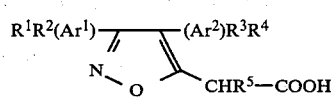

and pharmaceutically acceptable salts thereof in which $Ar^1$ and $Ar^2$ are the same or different and are selected from phenyl and naphthyl, $R^1$, $R^2$, $R^3$ and $R^4$ are the same or different substituents attached to $Ar^1$ and $Ar^2$, respectively, and are selected from hydrogen, halogen, trifluoromethyl, lower alkyl, and lower alkoxy, and $R^5$ is selected from hydrogen, lower alkyl, and lower alkoxy, with the term "lower" denoting the presence of 1–4 carbon atoms in a straight or branched chain.

2. A compound according to claim 1 wherein $R^1$, $R^2$, $R^3$, and $R^4$ are hydrogen, trifluoromethyl, lower alkyl, or lower alkoxy.

3. A compound according to claim 2 wherein $R^1$ and $R^3$ are hydrogen.

4. A compound according to claim 3 where $R^5$ is hydrogen or methoxy.

5. A compound according to claim 4 where $R^2$ and $R^4$ are both hydrogen or are both methoxy and $Ar^1$ and $Ar^2$ are both phenyl.

6. A compound according to claim 1 where $R^1$ and $R^3$ are both hydrogen.

7. A compound according to claim 6 where $Ar^1$ and $Ar^2$ are both phenyl.

8. A compound according to claim 7 where $R^2$ and $R^4$ are hydrogen, lower alkyl, or lower alkoxy.

9. A compound according to claim 8 where $R^2$ and $R^4$ are both hydrogen or both lower alkoxy.

10. A compound according to claim 9 where $R^5$ is hydrogen or methoxy.

11. 3,4-Diphenylisoxazol-5-acetic acid.

12. 3,4-Di(p-methoxyphenyl)isoxazol-5-acetic acid.

13. 3,4-Di(p-methoxyphenyl)isoxazol-5α-methoxyacetic acid.

14. Sodium 3,4-di(p-methoxyphenyl)isoxazol-5α-methoxyacetate.

15. A process for preparing a compound of the formula 1

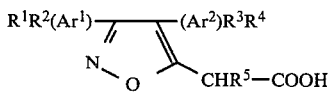

and pharmaceutically acceptable salts theory in which $Ar^1$ and $Ar^2$ are the same or different and are selected from phenyl and naphthyl, $R^1$, $R^2$, $R^3$ and $R^4$ are the same of different substituents attached to $Ar^1$ and $Ar^2$, respectively, and are selected from hydrogen, halogen, trifluoromethyl, lower alkyl, and lower alkoxy, with the term "lower" denoting the presence of 1–4 carbon atoms in a straight or branched chain, which comprises treating an aryl-(aryl-substituted methyl)-ketone of the formula 2

$$R^1R^2(Ar^1)-CO-CH_2-(Ar^2)R^3R^4 \quad 2$$

in which $R^1$, $R^2$, $R^3$, $R^4$, $Ar^1$, and $Ar^2$ are as defined above with hydroxylamine in the presence of a strong base to obtain the corresponding oxime of formula 3

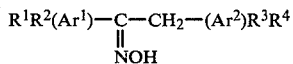

in which $R^1$, $R^2$, $R^3$, $R^4$, $Ar^1$, and $Ar^2$ are as defined above, treating said last-named oxime with two molar equivalents of n-butyllithium followed by treatment with a lower alkyl ester of an acid of the formula $R^5COOAlk$ in which $R^5$ is selected from hydrogen and lower alkoxy and Alk is lower alkyl, to obtain the corresponding isoxazole of the formula 4

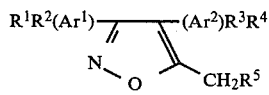

in which $R^1$, $R^2$, $R^3$, $R^4$, $Ar^1$, and $Ar^2$ are as defined above and $R^5$ is selected from hydrogen and lower alkoxy, treating said last-named compound with 1.0–1.1 molar equivalents of n-butyllithium followed by treatment with solid carbon dioxide, and isolating the corresponding compound of formula 1 in which $R^1$, $R^2$, $R^3$, $R^4$, $Ar^1$, and $Ar^2$ are as defined above and $R^5$ is selected from hydrogen and lower alkoxy; and, when it is desired to obtain a compound of formula 1 in which $R^5$ is lower alkyl, treating a compound of formula 1 in which $R^1$, $R^2$, $R^3$, $R^4$, $Ar^1$, and $Ar^2$ are as defined above and $R^5$ is hydrogen with two molar equivalents of n-butyllithium followed by treatment with a lower alkyl halide in which the halogen has an atomic weight greater than 19, and isolating the corresponding compound of formula 1 in which $R^1$, $R^2$, $R^3$, $R^4$, $Ar^1$, and $Ar^2$ are as defined above and $R^5$ is lower alkyl.

16. A process as claimed in claim 15 in which the compound of formula 1 in which $R^1$, $R^2$, $R^3$, $R^4$, $Ar^1$, and $Ar^2$ are as defined in the first instance is converted to a pharmaceutically acceptable salt thereof.

17. A process as claimed in claim 15 in which the compound of formula 2 is desoxybenzoin, the compound of formula 3 is desoxybenzoin oxime, the lower alkyl ester of an acid is ethyl acetate, the compound of formula 4 is 3,4-diphenyl-5-methylisoxazole, and the compound of formula 1 is 3,4-diphenylisoxazol-5-acetic acid.

18. A process as claimed in claim 15 in which the compound of formula 2 is desoxyanisoin, the compound of formula 3 is desoxyanisoin oxime, the lower alkyl ester of an acid is ethyl acetate, the compound of formula 4 is 3,4-di(p-methoxyphenyl)-5-methylisoxazole, and the compound of formula 1 is 3,4-di(p-methoxyphenyl)isoxazol-5-acetic acid.

19. A process as claimed in claim 15 in which the compound of formula 2 is desoxyanisoin, the compound of formula 3 is desoxyanisoin oxime, the lower alkyl ester of an acid is methyl methoxyacetate, the compound of formula 4 is 3,4-di(p-methoxyphenyl)-5-methoxymethylisoxazole, and the compound of formula 1 is 3,4-di(p-methoxyphenyl)isoxazol-5α-methoxyacetic acid.

20. A process as claimed in claim 19 which comprises the further steps of treating 3,4-di(p-methoxyphenyl)-5α-methoxyacetic acid with one molar equivalent of sodium 2-ethylhexanoate and isolating sodium 3,4-di p-methoxyphenyl)-isoxazol-5α-methoxyacetate.

21. A process as claimed in claim 15 in which
 (a) the ketone of formula 2 is stirred in an inert solvent with hydroxylamine hydrochloride, a strong base is slowly added, the mixture is heated, the solvent evaporated, the residue washed, to obtain the corresponding oxime of formula 3;
 (b) said oxime of formula 3 in solution in an inert solvent is agitated at −50° C. to 5° C. with two molar equivalents of n-butyllithium for 10-60 minutes, one-half molar equivalent of a lower alkyl ester of an acid of the formula $R^5CH_2COOAlk$ in which $R^5$ is selected from hydrogen and lower alkoxy and Alk is lower alkyl is added, the mixture is agitated at −5° C. for 10–120 minutes, acidified with a mineral acid, heated to 50° C. to 150° C. for 1–3 hours, and the aqueous phase is separated, to obtain the corresponding compound of formula 4 in which $R^5$ is hydrogen or lower alkoxy;
 (c) said compound of formula 4 in solution in an inert solvent is agitated at −75° C. to −50° C. with 1.0–1.1 molar equivalents of n-butyllithium for 1–3 hours, the mixture contacted with solid carbon dioxide, allowed to come to ambient temperature, diluted with water, acidified with a mineral acid and extracted with a water-immiscible solvent, to obtain the corresponding compound of formula 1 in which $R^5$ is selected from hydrogen and lower alkoxy.

22. A process as claimed in claim 21 in which the compound of formula 1 in which $R^5$ is hydrogen in solution in an inert solvent is agitated at a temperature below −20° C. with 2 molar equivalents of n-butyllithium for 20–60 minutes, 1.2–1.7 molar equivalents of a lower alkyl halide in which the halogen has an atomic weight greater than 19 are added with agitation for 1–3 hours, the mixture is acidified with a mineral acid and extracted with a water-immiscible solvent, to obtain the corresponding compound of formula 1 in which $R^5$ is alkyl.

23. A process as claimed in claim 22 and in which $R^2$ and $R^4$ are selected from hydrogen and the same or different lower alkyl and lower alkoxy, $R^1$ and $R^3$ are both hydrogen.

24. A process as claimed in claim 22 in which $Ar^1$ and $Ar^2$ are both phenyl, $R^2$ and $R^4$ are both hydrogen or both lower alkoxy, $R^1$ and $R^3$ are both hydrogen.

* * * * *